(12) United States Patent
Schnell

(10) Patent No.: US 8,251,068 B2
(45) Date of Patent: Aug. 28, 2012

(54) INSERTION AID FOR PERCUTANEOUS TRACHEOSTOMY

(75) Inventor: Ralf Schnell, Seligenstadt (DE)

(73) Assignee: Tracoe Medical GmbH, Frankfurt (DE)

( * ) Notice: Subject to any disclaimer, the term of this patent is extended or adjusted under 35 U.S.C. 154(b) by 1342 days.

(21) Appl. No.: 11/912,239

(22) PCT Filed: Mar. 30, 2006

(86) PCT No.: PCT/EP2006/061184
§ 371 (c)(1), (2), (4) Date: Oct. 22, 2007

(87) PCT Pub. No.: WO2006/120077
PCT Pub. Date: Nov. 16, 2006

(65) Prior Publication Data
US 2008/0142005 A1   Jun. 19, 2008

(30) Foreign Application Priority Data
May 10, 2005   (DE) .......................... 10 2005 021 470

(51) Int. Cl.
*A61M 16/00* (2006.01)
(52) U.S. Cl. ..................... 128/207.29; 606/190; 606/191
(58) Field of Classification Search ............. 128/207.29, 128/207.14, 207.15; 604/110, 111, 158, 604/192; 606/184, 185, 190, 191
See application file for complete search history.

(56) References Cited

U.S. PATENT DOCUMENTS
3,626,950 A * 12/1971 Schulte ......................... 604/268
(Continued)

FOREIGN PATENT DOCUMENTS
CA   1324555   11/1993
(Continued)

*Primary Examiner* — Thomas Barrett
*Assistant Examiner* — Si M Lee
(74) *Attorney, Agent, or Firm* — Paul and Paul

(57) ABSTRACT

A device for inserting a tracheal tube into a tracheostomy has as insertion aid with a shaft (6, 6', 14) which can be inserted through the tracheal tube, and a conical tip (2, 13) which is or can be joined to the tracheal tube. In order to provide a device for inserting a tracheal tube which considerably reduces the risk of injury when inserting the tracheal tube, which makes the insertion process easier, the inserted tube being highly comfortable even with a long-term use, keeping low the danger of injuries or sore points in the trachea, the insertion aid according to the invention has a conical tip (2, 13) which can have a small base diameter in a first state and a large base diameter in a second state. The insertion aid includes a section (6', 14) adjacent to the conical tip (2) whose diameter corresponds at the most to the inner diameter of a tracheal tube (1) to be inserted by means of the insertion aid, the small base diameter of the conical tip also being at the most equal to the inner diameter of the tracheal tube, while the large base diameter of the conical tip is larger than the inner diameter of the tracheal tube and preferably corresponds to approximately the outer diameter of the tracheal tube to be inserted with the insertion aid.

4 Claims, 3 Drawing Sheets

U.S. PATENT DOCUMENTS

| | | | |
|---|---|---|---|
| 4,278,081 A * | 7/1981 | Jones | 128/207.15 |
| 4,502,482 A | 3/1985 | DeLuccia et al. | |
| 4,637,388 A * | 1/1987 | Melendy | 128/207.14 |
| 5,015,240 A * | 5/1991 | Soproni et al. | 604/192 |
| 5,058,580 A * | 10/1991 | Hazard | 128/207.15 |
| 5,323,771 A | 6/1994 | Fisher et al. | |
| 5,347,078 A * | 9/1994 | Eckels | 588/249.5 |
| 5,653,230 A | 8/1997 | Ciaglia et al. | |
| 5,687,714 A | 11/1997 | Kolobow et al. | |
| 5,824,002 A | 10/1998 | Gentelia et al. | |
| 5,836,913 A * | 11/1998 | Orth et al. | 604/107 |
| 6,298,851 B1 * | 10/2001 | Parota et al. | 128/207.29 |
| 6,902,575 B2 * | 6/2005 | Laakso et al. | 623/1.11 |
| 7,294,136 B2 * | 11/2007 | Dubrul et al. | 606/185 |
| 7,534,250 B2 * | 5/2009 | Schaeffer et al. | 606/191 |
| 2004/0049222 A1 | 3/2004 | Schaeffer et al. | |

FOREIGN PATENT DOCUMENTS

| | | |
|---|---|---|
| DE | 7911837 | 7/1979 |
| DE | 3335715 A1 | 11/1985 |
| DE | 4115548 A1 | 11/1991 |
| DE | 68919842 | 5/1995 |
| DE | 69107376 | 6/1995 |
| DE | 69316604 | 8/1998 |
| DE | 69631337 | 12/2004 |
| DE | 69729339 | 6/2005 |
| EP | 1099451 A | 5/2001 |
| WO | 2004014234 A2 | 2/2004 |

* cited by examiner

INSERTION AID FOR PERCUTANEOUS TRACHEOSTOMY

CROSS REFERENCE TO RELATED APPLICATION

This application is the U.S. national phase under 35 U.S.C. 371 of PCT International Application No. PCT/EP2006/061184, filed on Mar. 30, 2006 and claiming priority to German application no. 10 2005 021 470.3, filed on May 10, 2005.

BACKGROUND OF THE INVENTION

1. Field of the Invention

The present invention relates to a device for introducing a tracheostomy tube into a tracheostoma with the help of an insertion aid which has a stem that can be guided through the tracheostomy tube and a conical tip that can be or is connected to the stem.

The tracheotomy is one of the oldest procedures in the history of medicine. The origins of this technique go back to antiquity. In a standard tracheotomy, artificial access to the trachea is surgically created below the larynx, typically between the $1^{st}$ and $2^{nd}$ or $2^{nd}$ and $3^{rd}$ tracheal rings. A so-called tracheostomy tube is fitted around this artificial opening to maintain respiration. Medical indications, such as e.g. the need for long-term respiration, make this technique still necessary today. As an alternative to surgery, minimally invasive puncture techniques have also been developed in recent decades. Thus in particular Ciaglia's percutaneous dilation tracheotomy, Griggs' dilation tracheotomy and Fantoni's translaryngeal tracheotomy are widely used.

2. Brief Description of the Prior Art

In Ciaglia's percutaneous dilation tracheotomy, the trachea is first punctured at a suitable point with a steel cannula. This procedure is usually carried out accompanied by broncho-scopic monitoring in order to prevent injury to the sensitive tracheal rear wall. The correct position of the cannula tip can checked by aspiration of air into a fitted-on syringe filled with liquid. If the position is correct, a teflon catheter located above the steel cannula is inserted 1 to 2 cm distally into the trachea. After the steel cannula is removed, a J-shaped guide wire (approx. 1.3 mm diameter) is advanced into the trachea through this teflon catheter. The teflon catheter can be removed afterwards. Instead, a tubular plastic catheter with a safety stop is then pushed over the guide wire for the purpose of reinforcement. One or several successive dilators can be pushed into the tracheal lumen over the reinforced guide wire with the help of a rotating movement to widen the puncture opening. Because of the conical shape of the dilators, the tissue spreads with the result that the tracheostomy tube wetted with lubricant can be inserted over the guide wire with the help of a special insertion aid (obturator). The correctness of the position is checked with the bronchoscope. The guide wire can then be removed and a balloon on the tracheostomy tube filled with air in order to seal off the trachea.

In Griggs' dilation tracheotomy, forceps are used instead of the conical dilators to spread the tissue.

In the minimally-invasive dilation technique, the laid tracheostoma is very narrow. In order to still be able to insert the tracheostomy tube, an insertion aid is used the tip of which is conically tapered similarly to the dilators. The insertion aid is a flexible rod or tube the length of which is such that it can be pushed fully through the lumen of the tracheostomy tube, with the result that the conical tip projects out of the tracheostomy tube at the distal end. In this state, the tracheostomy tube is inserted into the tracheostoma and pushed through constrictions, wherein the conical tip widens the constriction accordingly.

After the tracheostomy tube is inserted, the insertion aid must naturally be pulled out of the cannula again. This necessarily means that the diameter of the whole insertion aid, including the area of the conical tip, must be smaller than the internal diameter of the cannula. As the cannula must display a degree of stability, it also has a corresponding wall thickness of at least 0.5 to 1 mm. This in turn means that there is a stepped transition from the internal diameter to the external diameter of the cannula at the base of the conical tip of the insertion aid or, if the latter projects further over the distal end of the tracheostomy tube, at the corresponding stem section of the insertion aid. In other words, the distal end-surface of the tracheostomy tube is exposed. This in turn means that, specifically at constrictions of the tracheostoma, although the conical tip initially widens the diameter to the internal diameter of the cannula, the remaining widening must be created by the end-surface of the tracheostomy tube, which is not really designed for this. This can sometimes lead to injuries and in any event makes it much more difficult to insert the cannula.

FIG. 1 illustrates this situation with the help of the schematic representation of the distal end of a tracheostomy tube 1 from which the conical tip 8 of an insertion aid projects, wherein however the end-surface edge 9 of the tracheostomy tube 1 is exposed and makes the insertion much more difficult, in particular at constrictions of the tracheostoma.

Specifically in the case of cannulas with thick walls, this sudden transition can be a real problem. Thus, when trying to insert the cannula, the doctor often snags the cannula wall on a tracheal ring. This can result in a fracture of the cricoid cartilage.

Although the edge 9 of the tracheostomy tube 1 could also be chamfered in extension of the conical tip 8, this means that after the insertion aid, and thus also the conical tip 8, is removed a relatively sharp-edged internal edge forms the distal end of the tracheostomy tube 1 which in turn can cause injuries or wounds if it comes into contact with the sensitive trachea and thereby also cause pain which would make the long-term wearing of such a tracheostomy tube even more unpleasant for a patient.

SUMMARY OF THE INVENTION

Compared with this state of the art, the object of the present invention is to create a device for the introduction of a tracheostomy tube with the features named at the outset which significantly reduces the risk of injury during the introduction of the tracheostomy tube and facilitates the insertion procedure, wherein the thus-inserted cannula, even if used long-term, has a high wearing comfort and keeps the risk of injuries or wounds in the trachea low.

This object is achieved in that the device has a conical tip which can be changed into a state with a small base diameter and into a state with a large base diameter, wherein in the state with a small base diameter the diameter of the conical tip, and also of the adjacent section, is at most equal to the internal diameter of the tracheostomy tube, with the result that in this state the insertion aid can be pulled back through the tracheostomy tube, while in the state with a large base diameter the base of the conical tip at least partly covers the distal end-surface of the tracheostomy tube because the diameter of the base is larger in this state than the internal diameter of the tracheostomy tube and preferably approximately corresponds to the external diameter of the tracheostomy tube.

Both the state with a small base diameter and the state with a large base diameter can be set as required.

In this case, the term "conical" is not to be understood in the strictly geometric sense, but relates essentially to a diameter which increases from the tip to the base without any sudden widenings, wherein the contour of the "cone" can be curved concave or convex throughout.

Moreover, the term "base" applied to the conical tip initially relates literally only to the lower plane of the conical tip which has the maximum cone diameter and which determines the extent of the covering of the distal end-surface of the cannula. However, depending on the context, the term "base" optionally also covers the lower section, adjoining this level, of the cone provided that before passing the cone through the cannula its diameter in the state with a large base diameter is likewise even larger than the internal diameter of the cannula. To withdraw the insertion aid through the cannula, this area (in the state of the base with a small diameter) must also encompass a diameter which corresponds at most to the internal diameter of the cannula.

In the state of the conical tip with a small base diameter, such an insertion aid is initially introduced into the tracheostomy tube from the proximal side, wherein the conical tip is changed into the state with a large base diameter at the latest when it has been passed through the cannula to the distal end, with the result that the conical tip has emerged completely from the distal end. Alternatively, a correspondingly designed insertion aid can also be inserted from the distal end of the tracheostomy tube into same before being introduced into the tracheostoma. If inserted from the distal end, the conical tip can be in the state with a large base diameter from the outset. However, the proximal end must fit through the cannula with the stem of the insertion aid.

As a rule, actuation devices are provided at the proximal end of the insertion aid which are at least partly connected in one piece to the insertion aid and which are in general too large to fit through a tracheostomy tube, with the result that as a rule the insertion aid is inserted into the tracheostomy tube from the proximal side. In practice, a corresponding cannula with insertion aid can be supplied preassembled in a sterile pack.

In the state with a large base diameter of the conical tip, the tracheostomy tube is then inserted together with the insertion aid into the tracheostoma, wherein the conical tip ensures a careful widening and the tracheostoma widens to the full external diameter of the tracheostomy tube, with the result that the latter can be inserted correspondingly easily, does not snag on constrictions and also does not cause any additional injuries whatever.

Once the tracheostomy tube has been inserted and has reached its desired end position, the conical tip is changed into the state with a small base diameter, with the result that it can be withdrawn in this state through the tracheostomy tube, while the tracheostomy tube is held fast and remains in place. Naturally, the conical tip could also already be changed earlier into the state with a small base diameter if corresponding constrictions and in particular the cartilages of the larynx are pierced and the distal end of the cannula has reached the trachea. The further insertion of the cannula into the trachea into its final position can then also be carried out without the conical tip which could accordingly already be changed earlier into the state with a small base diameter and withdrawn.

In a preferred embodiment of the invention, at least the conical tip, more precisely at least the base of the conical tip, and the adjacent stem section of the insertion aid, can be made of an elastic material which, when corresponding forces are applied, can be expanded into the state with a large base diameter and, when the forces decrease, contract into the state with a small base diameter, because of the inherent elastic restoring forces. In the case of such an embodiment, the conical tip and the adjacent stem section is provided with a substantially central longitudinal bore, wherein a displacer is provided which has a much larger diameter than the central longitudinal bore (in the unloaded state) and which can be moved into this bore up to the area of the conical tip and also withdrawn again, with the result that when the displacer is pushed into the bore the conical tip is widened into the state with a large base diameter and after the displacer is withdrawn from this area of the bore the conical tip contracts again into the state with a smaller base diameter.

A similar embodiment has a conical tip divided into several sectors which are gripped and held together by an outer, elastic sleeve and are preferably also cohere closely on the tip of the cone. For their part, the individual sector elements enclose a cavity which as before can be widened by a corresponding displacer, wherein the individual sectors can be pushed outwards and in the process expand the outer elastic sleeve until the whole of the conical tip has achieved the state with a large diameter. After withdrawal of the displacer, the elastic sleeve ensures that the individual sector elements are pressed together again, with the result that the whole of the conical tip has achieved a state with a small diameter.

In the case of such an embodiment, the section, adjacent to the conical tip, of the stem of the insertion aid need not be elastically expandable as such, but can have a constant, unchanging diameter which corresponds at most to the internal diameter of the cannula.

According to a further embodiment of the invention, the conical tip consists of an inner core and an outer sleeve of a flexible material, wherein sleeve and core cohere at the front end of the conical tip and wherein on the base of the conical tip the outer sleeve has a radial thickness which corresponds at least approximately to half the wall thickness of the associated tracheostomy tube or is also optionally somewhat larger, whereas the core has a maximum diameter which is at most equal to the internal diameter of the tracheostomy tube. This core is connected to a flexible stem by which the core of the tracheostomy tube can be withdrawn into the inside of the cannula. As the tip of the core is joined to the outer, elastic sleeve, by withdrawing the core the conical tip is turned in, while the base of the outer elastic sleeve rests as before on the front edge of the tracheostomy tube. The inside surface of the outer elastic sleeve rests against the outer surface of the core and the sleeve can contract ever further when the core is withdrawn, as the base of the outer sleeve rests against core areas with an increasingly smaller diameter while the core is withdrawn. Finally a state is reached in which the core is withdrawn so far that the external diameter of the base of the outer sleeve lying against the core of the conical tip is smaller than the internal diameter of the tracheostomy tube. In this state, when the core is withdrawn further the sleeve also slides along with it into the tracheostomy tube and the insertion aid can then be completely withdrawn from the cannula. The procedure when introducing the tracheostomy tube is practically the same as in the case of the initially described embodiment. Only the manner in which the conical tip is changed from the state with a large base diameter into a state with a small diameter differs from the previously described embodiment.

An advantage of variant described above is that the conical tip cannot under any circumstances snag on the distal end-surface of the cannula when withdrawing the stem and the core, as the outer sleeve, even if it initially lies with its base against the end-surface of the cannula and does not contract sufficiently to slip into the distal opening of the cannula in this alignment, it is ultimately fully inverted, with the result that the base surface then points in the opposite direction and the conical tip of the sleeve points in the direction of the distal cannula opening. In this state, the insertion aid can in every case be pulled with the inverted sleeve into the distal end of the cannula, wherein the sleeve is elastically compressed if need be.

In the case of the last-named embodiment, the core can naturally be made of a comparatively rigid and stiff material, while the sleeve, at least in the area of its base and the adjacent sections, must be sufficiently elastic so that, if the core correspondingly exposes the internal diameter, it contracts as a whole to a diameter, or can be compressed into a state, which corresponds at most to the internal diameter of the cannula.

In general, embodiments of the invention are preferred with which the insertion aid (including any actuation elements, provided they are arranged centrally, such as for example the displacer according to FIGS. 2 and 3) in each case has a central bore to house a guide wire. The insertion aid according to the invention is then even suitable to completely replace conventional dilators, because the conical tip of the insertion aid already acts as a dilator.

Further advantages, features and possible applications of the present invention become clear from the following description of a preferred embodiment and the corresponding figures. There are shown in:

DETAILED DESCRIPTION OF THE PREFERRED EMBODIMENTS

Figure 1:
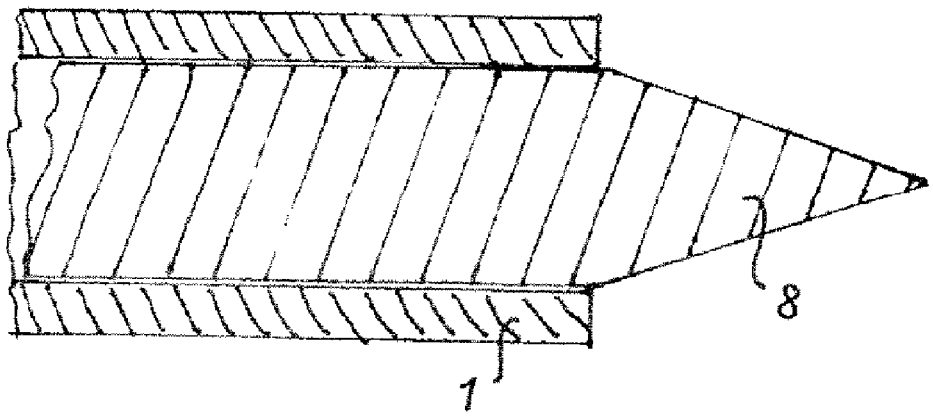
FIG. 1 an insertion aid with a tracheostomy tube according to the state of the art, FIG. 2 a first embodiment of the insertion aid according to the invention with a tracheostomy tube in a state with a large base diameter of the conical tip, FIG. 3 the embodiment according to FIG. 2 with a small diameter of the conical tip, FIG. 3a a detail view of the base of a conical tip of the insertion aid and of the distal end of a tracheostomy tube of a further, alternative embodiment similar to the embodiment shown in FIG. 2, FIG. 4 an embodiment with an inner core and an outer elastic sleeve which can be turned inwards by withdrawing the core, FIG. 5 the embodiment according to FIG. 4 with a partly withdrawn core and FIG. 6 the embodiment according to FIG. 4 with a core withdrawn sufficiently for the partly inverted outer sleeve to have at the base an external diameter which corresponds to the internal diameter of the cannula, FIG. 7 a variant of the embodiment shown in FIGS. 4-6 and FIG. 8 the variant according to FIG. 7 in a withdrawable state.

FIG. 1 shows in a longitudinal section the tracheostomy tube numbered 1, wherein an insertion aid in the form of a flexible plastic rod or preferably a plastic tube with a conical tip 8 extends through the inside of the tracheostomy tube and projects from the tracheostomy tube 1 at the distal end. As the conical tip 8 must be withdrawn after insertion of the cannula 1 and no possibility is provided of reducing this diameter, the diameter of the conical tip on the base corresponds approximately to the internal diameter of the tracheostomy tube 1, with the result that the end-surface 9 of the distal end of the tracheostomy tube, which must be inserted through the tracheostoma, is exposed.

It is understood that all the figures reproduce the individual elements and features only schematically and that for example the ratio of the wall thickness to the internal diameter of the tracheostomy tube 1 is exaggerated in these figures. In addition, the edges on the end-surfaces 9 of the tracheostomy tube 1 need not actually be formed sharp-edged with rectangular corners in cross-section, but can be rounded with a small radius. However, with the known insertion aids there is ultimately always a stepped transition from the base of the conical tip 8 or adjacent stem section of the insertion aid to the end-surface 9 of the tracheostomy tube 1.

Figure 2:
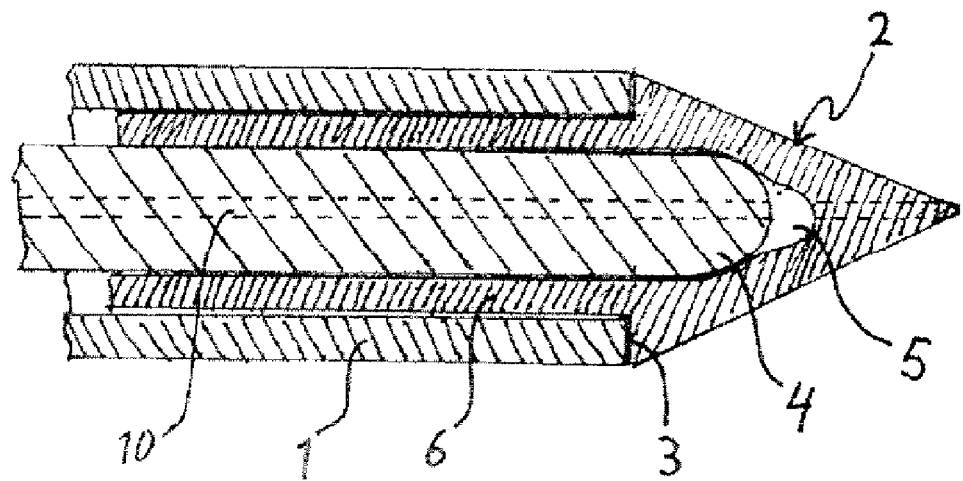
Figure 3:
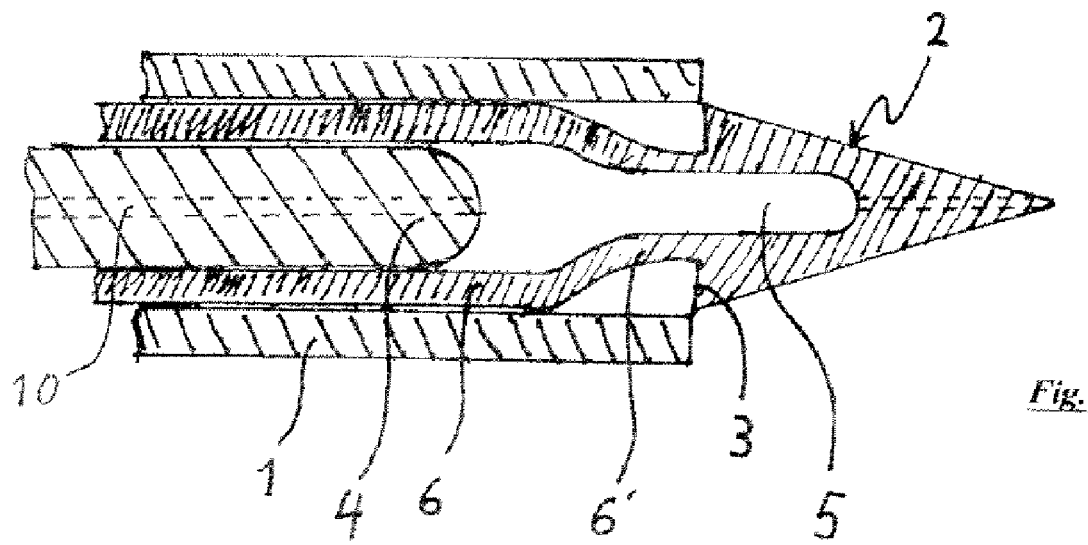

In contrast, FIG. 2 shows a first embodiment of the present invention in the state of the conical tip with a large base diameter. As can be seen, the insertion aid consists of a pipe- or tube-shaped stem 6 the central lumen or central bore 5 of which extends well into the conical tip 2 of the insertion aid and ends in the conical tip 2 as a blind bore or blind-end bore. FIG. 3 shows the same embodiment in a state of the conical tip 2 with a small base diameter.

As can be seen, a displacer 4 is arranged axially movable in the central bore 5. In the state shown in FIG. 3, this displacer 4 has been withdrawn some way into the stem 6 of the insertion aid, into an area of the stem 6 which, although it is sufficiently flexible to adapt to the shape of the tracheostomy tube, need not display any particular elasticity and therefore contracts to an inconsiderable extent, or not at all, when the displacer 4 is withdrawn into this area or out of this area. However, the front end 6' of the stem, which adjoins the base 3 of the conical tip 2, is made of a sufficiently elastic material and, in a state free from external forces, assumes the shape shown in FIG. 3 in which the diameter of the base 3 of the conical tip 2 is also at most equal to the internal diameter of the tracheostomy tube. By "external forces" are meant here not forces acting from the radially outer side of the insertion aid, but all forces which are not, like the elastic forces of the material of the insertion aid, inherent forces of same, but rather all forces which are inevitably exerted from outside the material of the insertion aid onto same. In particular, forces exerted by the displacer 4 onto the inner walls of the bore 5 are therefore "external forces" within the meaning outlined above. The state according to FIG. 3 is accordingly a state free from external forces or in short: a "force-free" state.

In practice, the diameter of the base 3 in the force-free state is chosen somewhat smaller than the internal diameter of the tracheostomy tube 1. If the tracheostomy tube 1 is to be introduced into a tracheostoma, the conical tip 2 must be in the state shown in FIG. 2. For this purpose, the displacer 4 is moved axially forward in the bore 5 into the conical tip 2. The flexible stem section 6', just like the whole base and the adjacent section of the conical tip, are widened because the diameter of the displacer 4 is much greater than the diameter of the bore 5 in the area of the conical tip 2 in the force-free state, as is shown in FIG. 3. Consequently, the diameter of the base 3 widens, wherein the displacer 4 and the bore 5 are dimensioned such that the base diameter in the state shown in FIG. 2 corresponds substantially to the external diameter of the tracheostomy tube.

Figure 3A:
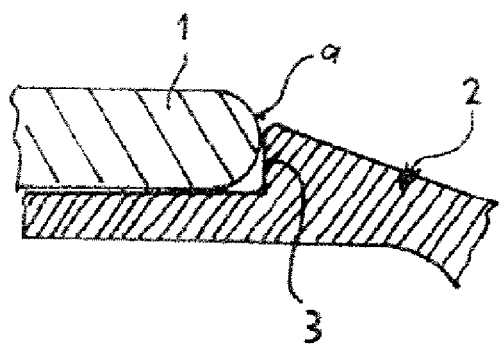

Irrespective of this, the outer edge of the distal end or the whole distal end-surface 9 of the tracheostomy tube 1 could be rounded, just like the outer edge of the base of the conical tip can also be somewhat rounded to facilitate the pulling of the conical tip into the distal opening of the tracheostomy tube and the withdrawal through the lumen of the tracheostomy tube. In this case, the diameter of the base of the conical tip need only correspond for example to the average value between internal and external diameter of the distal end of the cannula, or slightly more, as can be seen for example in a detailed view according to FIG. 3a. In this example, the outer part of the rounding of the end-surface 9 of the cannula 1 roughly follows the elongation of the conical course of the tip 2.

Furthermore, in FIGS. 2 and 3 dotted lines indicate a central bore 10 which is provided in a preferred variant of this embodiment. This bore 10, which is similarly also inherently present in the embodiments still to be described, serves to house a guide wire onto which the insertion aid can be pushed.

Figure 4:
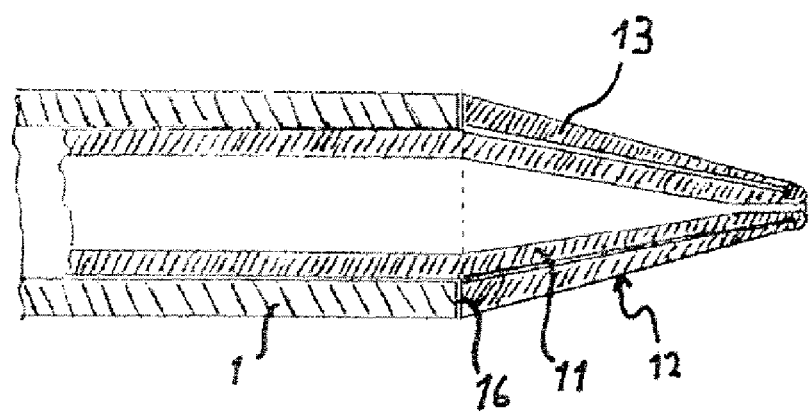
Figure 5:
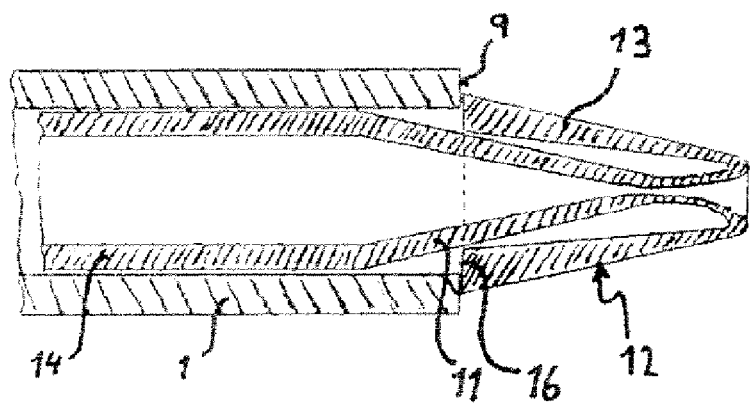
Figure 6:
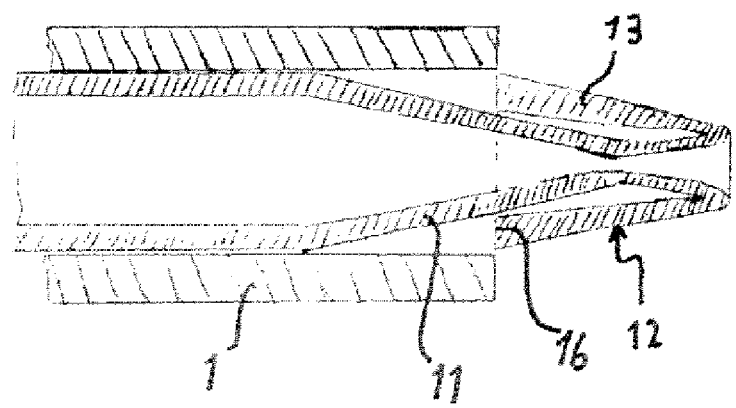

A further embodiment of a tracheostomy tube according to the invention is shown in FIGS. 4 to 6. In this case, the conical tip consists of an inner core 11 made of a relatively solid and stiff material and an outer sleeve 13 which is made of a very flexible, elastic material. The core 11 and the outer sleeve 13 cohere only at the front end of the conical tip, wherein in this state the tip has a somewhat rounded shape with a slight central recess, which does not, however, adversely affect its use if this tip has a sufficiently small diameter overall.

In the state shown in FIG. 4 the tracheostomy tube 1 is inserted into the tracheostoma in exactly the same way as described in connection with the insertion aid of the embodiment according to FIG. 2. The conical tip widens any constrictions, in particular in the area of the cartilages of the larynx, due to the gentle conical transition, until these constrictions are widened to the external diameter of the tracheostomy tube 1, with the result that the tracheostomy tube 1 can subsequently be pushed onward. Once the distal end of the tracheostomy tube 1 has reached the inside of the trachea or its final position, the insertion aid can be withdrawn by withdrawing the inner core 11 with the help of the adjacent stem 14 which is formed as a hose or flexible tube. The base 16 of the outer sleeve 13 rests on the end-surface 9 of the tracheostomy tube 1, with the result that the outer sleeve 13 must necessarily be turned in or inverted in the area of the conical tip. As the outer sleeve 13 is made of an elastic material, the base 16 meanwhile contracts in radial direction, as it is supported on its inside after withdrawal of the conical core 11 by core areas which have an ever-decreasing diameter. FIG. 5 shows an intermediate state of the inverting of the sleeve 13 and withdrawal of the core 11. In the state shown in FIG. 6, the core area 11 is withdrawn so far that the elastically contracting outer sleeve 13 [which] rests with its base 16 on an area of the core 11 which has a correspondingly small diameter, with the result that the external diameter of the base 16 of the sleeve 13 has now reached the value of the internal diameter of the tracheostomy tube 1. In this state, the insertion aid can be pulled through the tracheostomy tube 1 and out at the proximal end.

If the sleeve 13 does not contract sufficiently during the procedure just described, or the sleeve puckers or buckles eccentrically, with the result that the base 16 of the sleeve 13 stays in contact with the end-surface 9 of the cannula 1, this ultimately results, upon further withdrawal of the stem 14 and of the core 11, in the sleeve 13 being completely inverted. In this case, the base 16 of the sleeve points in the opposite direction to that shown in FIGS. 4 to 6 and the tip of the conical sleeve 13 likewise points in the opposite direction to that shown in FIG. 4. In this state, the sleeve 13 can also be pulled fully into the distal opening of the cannula 1, even if the external diameter of the base 16 of the elastic sleeve 13 should still be greater than corresponds to the internal diameter of the cannula 1. In this case, due to the conical outer surface of the sleeve 13, which was previously the inner surface of this sleeve and which comes into contact with the edge of the distal opening with the cannula 1, the sleeve 13 would be sufficiently compressed to be able to be pushed into the cannula 1 and withdrawn out of it at the proximal end.

Suitable handling equipment for the insertion aid or the proximal end of the shaft 6 or 14 follow in obvious manner from the described procedure for setting the different states of the conical tip and need not be described further here. For example, the proximal end of the shaft 6 or 14 could be provided with an annular gripping section in which a finger can be introduced in order to withdraw the insertion aid while the tracheostomy tube 1 is held in place. A corresponding actuator in the form of a gripping ring or similar can also be provided for the displacer 4 according to the embodiments of FIGS. 2 and 3. However, instead of a gripping ring, flanges or other devices could also be provided which facilitate the gripping of the insertion aids or the displacer.

Figure 7:
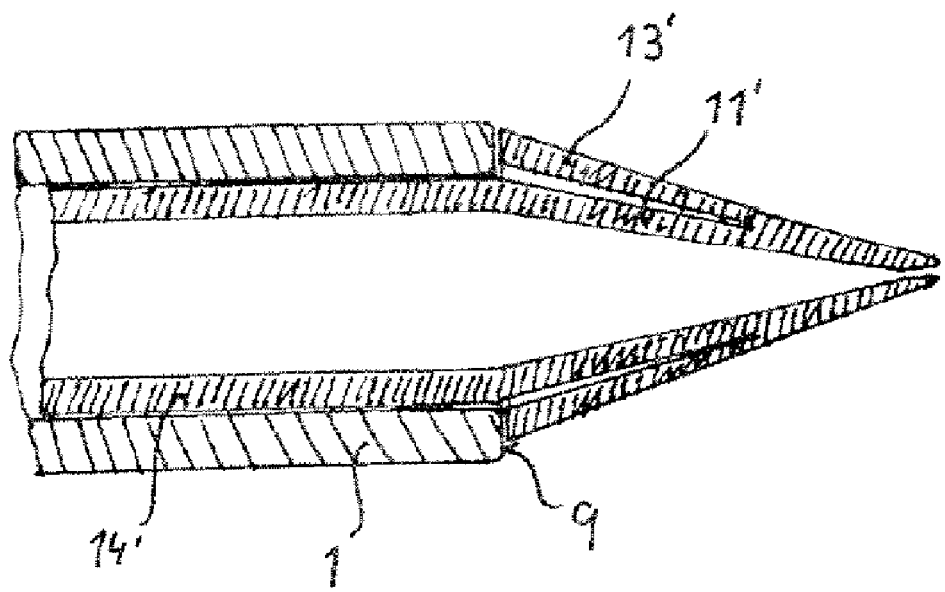
Figure 8:
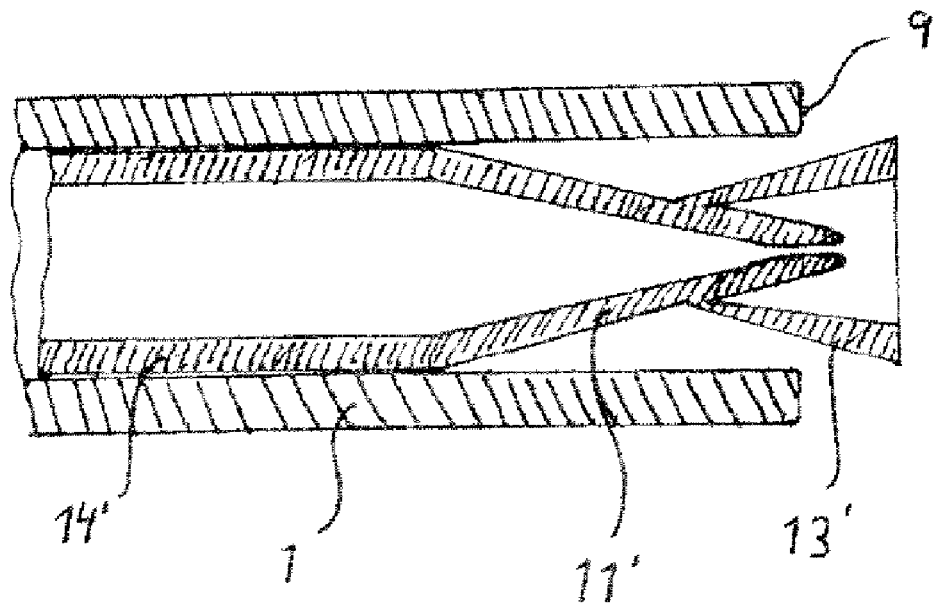

A variant of the embodiment shown in FIGS. 4 to 6 is shown in FIGS. 7 and 8. In this case, the outer sleeve 13' does not rest on the tip of the conical core 11', but is at a distance from this tip. However, the procedure for this embodiment is the same as described in connection with FIGS. 4 to 6. Here also, the representation is only schematic and any graphical inaccuracies in respect of the dimensions and exact positioning of individual elements in FIGS. 7 and 8 (just as also in the previously described figures) are not to be interpreted as contrary to the statements of the description and claims. Thus for example in the state shown in FIG. 7 the base of the outer sleeve 13' lies tight against the inner conical core 11', due to its elasticity, even if, in order to highlight the two elements as parts movable against each other, there seems to be a distance between the base of the sleeve and the core in the drawing. As the sleeve 13' is formed axially shorter compared with the sleeve 13 of FIGS. 4 to 6 and rests against a section of the cores 11' with a larger diameter, compared with the embodiment according to FIGS. 4 to 6 it tends more, when the stem 14 is withdrawn into the cannula 1, to become fully inverted or turned in, as is shown in FIG. 8.

For the purposes of original disclosure, it is pointed out that all the features as are revealed to a person skilled in the art from the present description, drawings and claims, although they have been specifically described only in connection with certain further features, can be combined both individually and in any configurations with other features or groups of features disclosed here, provided this has not been expressly excluded or technical circumstances do not make such combinations impossible or pointless. A comprehensive, explicit representation of all conceivable combinations of features is dispensed with here merely for the sake of brevity and readability of the description.

The invention claimed is:

1. A device which aids in the insertion of a tracheostomy tube into a tracheostoma, the tracheostomy tube having a wall thickness equal to the difference between an internal diameter and an external diameter of the tracheostomy tube, said insertion aid device comprising:
    a stem (6, 6', 14) that can be passed through the tracheostomy tube and a conical tip (2, 13) that can be or is connected to the stem,
    wherein the conical tip (2, 13) can be changed into a first state with a small base diameter and a second state with a large base diameter,
    wherein the stem has a section (6', 14) adjacent to the conical tip (2), said section having a diameter which corresponds at most to the internal diameter of a the tracheostomy tube (1);

wherein the small base diameter of the conical tip is likewise at most equal to the internal diameter of the tracheostomy tube whereas the large base diameter of the conical tip is greater than the internal diameter of the tracheostomy tube and corresponds approximately to the external diameter of the tracheostomy tube; and wherein the conical tip further comprises:

an inner core (11, 11') and an outer sleeve (13, 13'), wherein the outer sleeve (13) and inner core (11) are connected to each other;

wherein the outer sleeve has an external base diameter and a radial thickness which corresponds approximately to the wall thickness of a front end of the tracheostomy tube;

wherein the inner core (11, 11') has a maximum diameter which is smaller than or equal to the internal diameter of the tracheostomy tube (1), and wherein the inner core (11, 11') is connected to the stem (14, 14');

wherein retracting the stem causes the outer sleeve to be at least partially inverted from a point of attachment to the inner core (11, 11') due to its elastic pre-tension and contracts the outer sleeve until the external base diameter is approximately equal to or smaller than the internal diameter of the tracheostomy tube, allowing the conical tip to be withdrawn through the tracheostomy tube; and wherein the insertion aid device has a central bore to house a guide wire.

2. The device according to claim 1, wherein the outer sleeve (13') and inner core (11') are connected to each other at a distance from an end of the conical tip which corresponds to approximately ¼ to ½ of an axial length of the inner core.

3. The device according to claim 1 or 2, wherein the inner core (11') and the outer sleeve (13') are designed and connected to each other such that retracting the stem (14') causes the outer sleeve (13') to be completely inverted allowing the conical tip to be withdrawn through the tracheostomy tube.

4. A device for inserting a tracheostomy tube, having a front end, into a tracheostoma, said device having a stem that can be passed through the tracheostomy tube, and a conical tip that can be or is connected to the stem, characterized in that the conical tip can be changed into a first state with a small base diameter and into a second state with a large base diameter, wherein there is included a section adjacent to the conical tip the diameter of which corresponds at most to the internal diameter of the tracheostomy tube, and wherein the first state small base diameter of the conical tip is at most equal to the internal diameter of the tracheostomy tube, whereas the second state large base diameter of the conical tip is greater than the internal diameter of the tracheostomy tube and approximately corresponds to the external diameter of the tracheostomy tube, whereby the conical tip further includes an inner core and an outer sleeve, wherein the outer sleeve and the inner core are connected to each other on or adjacent to the conical tip, and wherein the outer sleeve on the base of the conical tip has a radial thickness which corresponds approximately to the wall thickness of the tracheostomy tube at its front end, and wherein the inner core has in the area of the base of the conical tip of a maximum diameter which is smaller than or equal to the internal diameter of the tracheostmy tube, and wherein the inner core is connected to a flexible stem or traction element which extends through the tracheostomy tube, wherein the effect of an exertion of traction on the traction element against a direction predetermined by the conical tip is that the sleeve supported on the front end of the tracheostomy tube is inverted from the point of attachment to the inner core and contacts due to its elastic pre-tension until its external diameter is approximately equal to or smaller than the internal diameter of the tracheostomy tube, with a result being that the conical tip with an at least partially inverted outer sleeve can be withdrawn through the tracheostomy tube, and wherein the device also includes a central bore to house a guide wire.

\* \* \* \* \*